United States Patent [19]

Woods et al.

[11] 3,966,816

[45] June 29, 1976

[54] 3-HALO-2,6-DINITRO-4-TRIFLUOROMETHYLANILINE

[75] Inventors: William G. Woods, Fullerton; Don L. Hunter, Anaheim, both of Calif.

[73] Assignee: United States Borax & Chemical Corporation, Los Angeles, Calif.

[22] Filed: Mar. 5, 1974

[21] Appl. No.: 448,322

Related U.S. Application Data

[63] Continuation-in-part of Ser. No. 878,262, Nov. 19, 1969, abandoned.

[52] U.S. Cl. .............................. 260/573; 260/577; 260/269; 260/293.51; 260/313.1; 260/239 A; 260/239 E
[51] Int. Cl.² .................. C07C 87/58; C07C 87/60
[58] Field of Search ............................ 260/573, 577

[56] References Cited

UNITED STATES PATENTS

| | | | |
|---|---|---|---|
| 2,212,825 | 8/1940 | Daudt et al. | 260/573 X |
| 3,518,309 | 6/1970 | Soper | 260/577 |
| 3,546,295 | 12/1970 | Marauetz | 260/577 |
| 3,661,889 | 5/1972 | Lange et al. | 260/573 X |
| 3,672,864 | 6/1972 | Marauetz | 260/577 X |
| 3,681,425 | 8/1972 | Kiehs et al. | 260/577 X |

*Primary Examiner*—Paul F. Shaver
*Attorney, Agent, or Firm*—James R. Thornton

[57] ABSTRACT

3-Halo-2,6-dinitro-4-trifluoromethylanilines having hydrocarbon substituents on the nitrogen atom. The hydrocarbon substituents can be alkyl, alkenyl, alkynyl or a portion of a heterocyclic group. The compounds are especially useful as intermediates for preparing herbicidal dinitro-1,3-phenylenediamines.

10 Claims, No Drawings

3-HALO-2,6-DINITRO-4-TRIFLUOROMETHYLANILINE

This is a continuation-in-part of our copending application Ser. No. 878,262 filed Nov. 19, 1969, now abandoned.

This invention relates to novel 3-halo-2,6-dinitro-4-trifluoromethylanilines of the formula

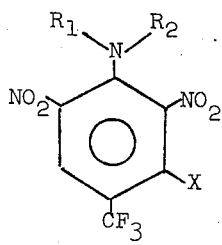

wherein X is a halogen atom such as bromo, chloro, iodo or fluoro, $R_1$ is hydrogen, alkyl, alkenyl, or alkynyl and $R_2$ is alkyl, alkenyl or alkynyl. Also, $R_1$-$R_2$ can represent a portion of a cyclic group such as an alkylene chain to form a heterocyclic group containing carbon atoms in addition to the nitrogen atom which is the point of attachment to the aromatic ring.

Typical examples of groups represented by $R_1$ and $R_2$, as defined above, are the lower alkyl, lower alkenyl, and lower alkynyl groups having up to about 6 carbon atoms, including the cyclic analogues thereof, as well as the halo, hydroxy, and lower alkoxy derivatives thereof. Representative groups are methyl, ethyl, n-propyl, isopropyl, n-butyl, sec-butyl, n-pentyl, sec-pentyl, n-hexyl, allyl, 2-butenyl, 2-butynyl, 3-butynyl, methallyl, 2-pentynyl, 2-hydroxyethyl, 2-bromoethyl, 2-methoxyethyl, 3-ethoxypropyl, 2,2-dimethoxyethyl, 2-chloroallyl, 3-chloropropyl, 4-hydroxy-2-butynyl, 1-methyl-2-methoxyethyl, 2-bromoallyl, propynyl, 4-chloro-2-butenyl, 3-bromo-1-butenyl, 3-iodo-2-pentenyl, 4-chloro-2-butynyl, cyclohexyl, cyclopropyl, cyclobutyl, cyclohexenyl, and the like.

Also, as described above, $R_1$-$R_2$ can represent a fragment of a ring of which the amino nitrogen is a part thereof such as illustrated by the structure —N⟨Z in which Z is an alkylene group having from about 2 to 6 carbon atoms in the chain, and optionally containing other atoms such as oxygen and nitrogen. Examples of such linkages include the dimethylene, trimethylene, tetramethylene, diethyleneoxy, diethyleneimino, and hexamethylene groups.

Representative examples of compounds of this invention are:

N-ethyl-3-chloro-2,6-dinitro-4-trifluoromethylaniline
N,N-dipropyl-3-chloro-2,6-dinitro-4-trifluoromethylaniline
N,N-dimethylene-3-chloro-2,6-dinitro-4-trifluoromethylaniline
N,N-diethyl-3-bromo-2,6-dinitro-4-trifluoromethylaniline
N-allyl-3-chloro-2,6-dinitro-4-trifluoromethylaniline
N-(3-chloropropyl)-3-chloro-2,6-dinitro-4l -trifluoromethylaniline
N-sec-butyl-3-fluoro-2,6-dinitro-4-trifluoromethylaniline
N-(1-methyl-2-methoxyethyl)-3-chloro-2,6-dinitro-4-trifluoromethylaniline
N,N-pentamethylene-3-chloro-2,6-dinitro-4-trifluoromethylaniline
N-n-hexyl-3-chloro-2,6-dinitro-4-trifluoromethylaniline
N-methyl-N-propyl-3-bromo-2,6-dinitro-4-trifluoromethylaniline
N,N-diallyl-3-fluoro-2,6-dinitro-4-trifluoromethylaniline
N-methyl-N-cyclopentyl-3-chloro-2,6-dinitro-4-trifluoromethylaniline
N-propynyl-3-bromo-2,6-dinitro-4-trifluoromethylaniline
N,N-bis(2-hydroxyethyl)-3-chloro-2,6-dinitro-4-trfluoromethylaniline
N-(2-hydroxyethyl)-N-methyl-3-chloro-2,6-dinitro-4-trifluoromethylaniline
N,N-diethyl-3-chloro-2,6-dinitro-4-trifluoromethylaniline The compounds of this invention are either crystalline solids or high-boiling liquids. Generally, they are only slightly soluble in water and are moderately soluble in the usual organic solvents such as ethanol, acetone, and benzene. The compounds are readily prepared by reaction of an amine with a 2,4-dihalo-3,5-dinitrobenzotrifluoride according to the equation

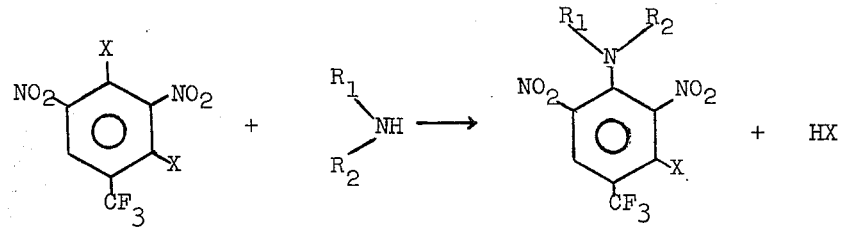

in which X is halogen, and $R_1$ and $R_2$ have the significance previously assigned.

The reaction is advantageously carried out in the presence of a solvent such as a hydrocarbon or alcohol. An excess of amine, such as about two moles of amine for each mole of the benzotrifluoride, is preferably employed. The second mole of amine neutralizes the by-product hydrogen halide as it is formed. Alternatively, a tertiary amine can be used as an acid neutralizing agent. The reaction can be carried out in a sealed reaction vessel such as an autoclave or at atmospheric pressure in the presence of a solvent. A reaction temperature in the range of from about 20° to about 100°C. preferably is employed to give good yields of the desired product and a satisfactory rate of reaction. The by-product amine hydrohalide is removed by washing with water or by filtration from the solvent in which it is insoluble. The desired product is isolated and purified by well known procedures such as by recrystallization.

The following examples describe preparation of representative compounds of this invention, but it is to be understood that the invention is not to be limited to the specific examples given.

EXAMPLE I

N,N-di-n-propyl-3-chloro-2,6-dinitro-4-trifluoromethylaniline

A heavy walled glass reaction tube of approximately 50 ml. capacity was charged with 7.0 grams (0.023 mole) of 2,4-dichloro-3,5-dinitrobenzotrifluoride, 4.64 grams (0.0458 mole) of di-n-propylamine and 40 ml. of absolute ethanol. The tube was sealed and heated in an oil bath at 94°–99°C. for 98 hours. The cooled reaction mixture was then evaporated to dryness to give an oily residue which was extracted with boiling diethyl ether. The insoluble di-n-propylamine hydrochloride was removed by filtration and washed with additional ether. The combined ether filtrates were evaporated to give an oily orange residue which was dissolved in 100 ml. of absolute ethanol and decolorized with activated charcoal. The ethanol and volatiles were removed by evaporation under reduced pressure to give the product (6.77 grams) as a viscous reddish oil.

EXAMPLE II

N-sec-butyl-3-chloro-2,4-dinitro-6-trifluoromethylaniline

To a stirred mixture of 20 g. (0.0655 mole) of 2,4-dichloro-3,5-dinitrobenzotrifluoride and 150 ml. of absolute ethanol was added 9.58 g. (0.131 mole) of sec-butylamine, dropwise, over a period of about 15 minutes. The resultant solution was refluxed for two hours and the ethanol then removed by distillation under reduced pressure. The solid yellow residue was triturated with 300 ml. water to dissolve the sec-butylamine hydrochloride. The water insoluble product was isolated by filtration, washed with water, and then dissolved in 600 ml. of refluxing 95% ethanol. Upon cooling, the product crystallized. Filtration gave 20.4 g. of a yellow crystalline solid, melting at 90.5° – 91.5°C.

EXAMPLE III

N,N-diethyleneoxy-3-chloro-2,6-dinitro-4-trifluoromethylaniline

The compound was prepared by reacting 2,4-dichloro-3,5-dinitrobenzotrifluoride with morpholine in an ethanol-dioxane solvent mixture. After recrystallization from ethanol, the compound melts at 125.5° – 126.5°C.

EXAMPLE IV

N-(2-bromoethyl)-3-chloro-2,6-dinitro-4-trifluoromethylaniline

The compound was prepared by reacting 2,4-dichloro-3,5,dinitrobenzotrifluoride with 2-bromoethylamine in an ethanol solution. The resultant product melted at 88° – 92°C.

EXAMPLE V

N-(2-chloroallyl)-3-chloro-2,6-dinitro-4-trifluoromethylaniline

The compound was prepared by reacting 2-chloroallylamine with 2,4-dichloro-3,5-dinitrobenzotrifluoride in ethanol. After recrystallization from ethanol, the compound melts at 78° – 80°C.

EXAMPLE VI

N-cyclopropyl-3-chloro-2,6-dinitro-4-trifluoromethylaniline

The compound was prepared by reacting cyclopropylamine with 2,4-dichloro-3,5-dinitrobenzotrifluoride in cyclohexane to give the product having a melting point of 86° – 87°C.

EXAMPLE VII

N-(2-methoxyethyl)3-chloro-2,6-dinitro-4-trifluoromethylaniline

The compound was prepared by reacting 2-methoxyethylamine was 2,4-dichloro-3,5-dinitrobenzotrifluoride in cyclohexane to give the product melting at 106.5° – 107.5°C.

EXAMPLE VIII

N-propynyl-3-chloro-2,6-dinitro-4-trifluoromethylaniline

The compound was prepared by reacting propargylamine with 2,4-dichloro-3,5-dinitrobenzotrifluoride in cyclohexane to give the product melting at 86° – 87°C.

EXAMPLE IX

N,N-diethyl-3-chloro-2,6-dinitro-4-trifluoromethylaniline

The compound was prepared by reacting diethylamine with 2,4-dichloro-3,5-dinitrobenzotrifluoride in ethanol to give the product melting at 35° – 36°C.

The 2,4-dihalo-3,5-dinitrobenzotrifluoride starting materials are readily prepared by nitration of the corresponding 2,4-dihalobenzotrifluoride with a mixture of fuming nitric and fuming sulfuric acids at a temperature below about 80°C. Reference is made to a copending application of Don L. Hunter, Ser. No. 832,860, filed June 12, 1969, now U.S. Pat. No. 3,586,725 issued June 22, 1971, which describes and claims preparation of the 2,4-dihalo-3,5-dinitrobenzotrifluorides.

The compounds of this invention are useful as intermediates for the preparation of herbicidal trifluoromethyl-2,4-dinitro-1,3-phenylenediamine compounds. The phenylenediamines are prepared according to the following equation.

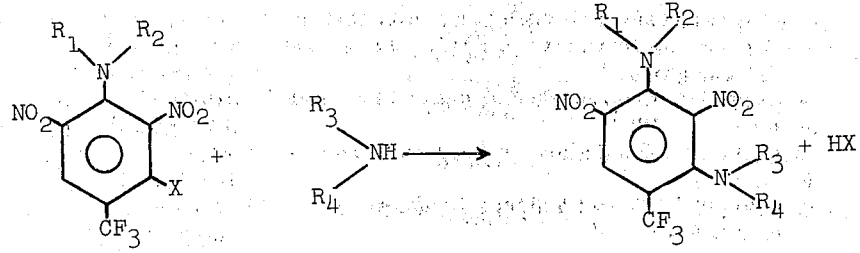

in which X, $R_1$ and $R_2$ have the significance previously assigned, and $R_3$ and $R_4$ are each selected from the group consisting of hydrogen, alkyl, alkenyl, and alkynyl. In the preparation procedure, the amine or ammonia is reacted with the compound of this invention either in a sealed reaction vessel such as an autoclave or at atmospheric pressure. The by-product hydrogen halide is neutralized by use of excess amine or a tertiary amine. Preferably a solvent such as an alcohol or hydrocarbon is employed to provide control of the reaction temperature which can be in the range from about 20° to about 120°C. The by-product amine hydrohalide is removed by washing with water or by filtration when a solvent is employed in which the hydrohalide is insoluble. The desired 1,3-phenylenediamine is isolated and purified by well known procedures.

The following example illustrates the use of the compounds of this invention as intermediates for preparing the herbicidal phenylenediamine compounds.

EXAMPLE X $N^3,N^3$-di-n-propyl-2,4-dinitro-6-trifluoromethyl-1,3-phenylenediamine A glass reaction tube was charged with 4.0 grams (0.0108 mole) of N,N-di-n-propyl-3-chloro-2,6-dinitro-4-trifluoromethylaniline, 5.82 grams (0.0237 mole) of 6.95% ethanolic ammonia and 35 ml. of ethanol. The tube was sealed and heated in an oven at 100°C. for 68 hours. The contents of the tube were cooled and the ethanol removed by evaporation. Water was added to the solid orange rsidue to dissolve the ammnium chloride and the insoluble produced was separated by filtration. The product was dissolved in refluxing 95% ethanol. Upon cooling, orange needles and a yellow powder crystallized. The yellow powder was identified as 2,4-dinitro-6-trifluoromethyl-1,3-phenylenediamine and was separated from the desired product by filtration after extracting with boiling hexane. The desired product dissolved in the hexane and was isolated from the filtrate by evaporation of the hexane. The residue was recrystallized from 95% ethanol to give orange needles, m.p. 124°–125°C.

Analysis: Calculated: N = 15.99 Found: N = 16.00.

The 1,3-phenylenediamine compounds are excellent herbicides and are especially useful as selective herbicides for controlling weeds in the presence of desirable crops such as corn, rice, cotton, and soybeans. Preparation of the 1,3-phenylenediamine compounds and their use as herbicides is claimed in the copending applications of Don L. Hunter et al., Ser. No. 812,307, filed Apr. 1, 1969, now abandoned and Ser. No. 875,508 filed Nov. 10, 1969, now U.S. Pat. No. 3,617,252.

Although the compounds of this invention are useful as intermediates for the production of 1,3-phenylenediamines which are excellent herbicides, they have very little herbicidal activity in their own right at commercially acceptable rates. Primary and secondary herbicidal screening results show that relatively high rates of application are required which would be commercially uneconomical. For example, the following results were obtained when the compounds were screened for pre-emergence and post-emergence activity at a rate of 5 pounds per acre.

PROCEDURE

Greenhouse flats of sterilized soil were planted to soybeans (SB), velvetleaf (VL), oats (O) and millet (M). The soil was a mixture of three parts sandy loam to two parts vermiculite. For the pre-emergence tests, the flats were sprayed on the same days as planting with an ethanol-dioxane solution of the compounds to be tested at a rate of 5 pounds per acre. For the post-emergence test, the flats were sprayed at the same rate when the plants had emerged and were about one inch in height (about 8 days). The flats were kept in the greenhouse and watered when needed. Nine and 21 days after treatment, the flats were examined and the plants rated for herbicidal activity using a 0–9 scale in which 0 = no effect, 2–3 = moderate injury; 5 = some kill; 7–8 = substantial kill and 9 = complete kill. The results obtained are shown in Table I.

TABLE I

| | Herbicidal Activity After | | | | | | | | | | | | | | | | |
|---|---|---|---|---|---|---|---|---|---|---|---|---|---|---|---|---|
| | 9 Days | | | | | | | | | 21 Days | | | | | | | |
| | | Pre | | | | Post | | | | | Pre | | | | Post | | |
| COMPOND | SB | VL | O | M | SB | VL | O | M | SB | | VL | O | M | SB | VL | O | M |
| N-(2-chloroallyl)-3-chloro-2,6-dinitro-4-trifluoromethylaniline | 0 | 0 | 0 | 0 | 0 | 0 | 0 | 0 | 0 | | 0 | 0 | 0 | 0 | 0 | 0 | 0 |
| N-(1-methyl-2-methoxyethyl)-3-chloro-2,6-dinitro-4-trifluoromethylaniline | 0 | 0 | 0 | 0 | 0 | 0 | 0 | 0 | 0 | | 0 | 0 | 0 | 0 | 0 | 0 | 0 |
| N-(3-pentyl)-3-chloro-2,6-dinitro-4-trifluoromethylaniline | 1 | 0 | 0 | 0 | 1 | 0 | 0 | 1 | 0 | | 0 | 0 | 0 | 1 | 4 | 0 | 1 |
| N-(propargyl)-3-chloro-2,6-dinitro-4-trifluoromethylaniline | 0 | 0 | 0 | 0 | 0 | 0 | 1 | 1 | 0 | | 0 | 0 | 0 | 0 | 0 | 0 | 1 |
| N,N-di-n-butyl-3-chloro-2,6-dinitro-4-trifluoromethylaniline | 0 | 0 | 0 | 0 | 0 | 0 | 0 | 0 | 0 | | 0 | 0 | 0 | 1 | 2 | 0 | 1 |
| N-methyl-N-(2-hydroxyethyl)-3-chloro-2,6-dinitro-4-trifluoromethylaniline | 0 | 0 | 0 | 0 | 0 | 2 | 0 | 1 | 0 | | 0 | 0 | 0 | 0 | 2 | 0 | 0 |
| N,N-pentamethylene-3-chloro-2,6-dinitro-4-trifluoromethylaniline | 0 | 0 | 0 | 0 | 0 | 0 | 0 | 0 | 0 | | 0 | 0 | 0 | 1 | 0 | 0 | 0 |
| N,N-diethyl-2,6-dinitro-3-chloro-4-trifluoromethylaniline | 0 | 0* | 0 | 0 | 0 | 0* | 0 | 0 | 0 | | 0** | 0 | 0 | 0 | 0** | 0 | 0 |
| N,N-di-n-propyl-3-chloro-2,6-dinitro-4-trifluoromethylaniline | 0 | 0* | 0 | 0 | 0 | 1* | 0 | 0 | 0 | | 0** | 0 | 0 | 1 | 1** | 0 | 0 |

\* after 8 days
\*\* after 22 days

The pre-emergence activity can be increased somewhat by incorporating the herbicide into the soil prior to planting. For example, the N,N-di-n-propyl-3-chloro derivative was tested in the same manner as a pre-emergence treatment at a one pound per acre rate, except the herbicide was incorporated by mixing into the top one inch of soil prior to planting a broad class of plant species. The results, 21 days after treatment, are shown in Table II. For comparison purposes, N,N-di-n-propyl-2,6-dinitro-4-trifluoromethylaniline of U.S. Pat. No. 3,257,190 was tested in the same manner and the plants rated sixteen days after treatment.

TABLE II

| Plant | Activity Rating | |
|---|---|---|
| | N,N-di-n-propyl-3-chloro-2,6-dinitro-4-trifluoro-methylaniline | N,N-di-n-propyl-2,6-dinitro-4-trifluoro-methylaniline |
| Pigweed | 3 | 9 |
| Crabgrass | 2 | 8 |
| Wild oats | 0 | 7 |
| Giant foxtail | 1 | 9 |
| Sorghum | 0 | 3 |
| Watergrass | 1 | 9 |
| Rice | 1 | 2 |
| Johnsongrass | 1 | 7 |
| Cotton | 1 | 0 |
| Barley | 1 | 2 |
| Soybeans | 1 | 1 |
| Corn | 1 | 0 |

In order to obtain significant herbicidal activity with the compounds of this invention, it is necessary to increase the rates to about 20 pounds per acre. For example, when the N,N-di-n-propyl-3-chloro- and N-(3-pentyl)-3-chloro-derivatives were applied to a broad class of plants at a rate of 20 pounds per acre in a pre- and post-emergence test, the following results were obtained 20 days after treatment.

TABLE III

| Plant Specie | N,N-di-n-propyl | | N-(3-pentyl) | |
|---|---|---|---|---|
| | Pre | Post | Pre | Post |
| Cucumbers | 2 | 7 | 2 | 3 |
| Watergrass | 9 | 6 | 8 | 8 |
| Crabgrass | 9 | 8 | 9 | 6 |
| Millet | 8 | 8 | 7 | 6 |
| Foxtail | 9 | 8 | 7 | 6 |
| Cotton | 0 | 2 | 0 | 0 |
| Bushbeans | 3 | 0 | 0 | 0 |
| Velvetleaf | 6 | 8 | 6 | 6 |
| Pigweed | 8 | 9 | 8 | 8 |

Similar results were obtained with other compounds of the invention at a rate of 20 pounds per acre.

Various changes and modifications of the invention can be made and to the extent that such variations incorporate the spirit of this invention, they are intended to be included within the scope of the appended claims.

What is claimed is:

1. A compound of the formula

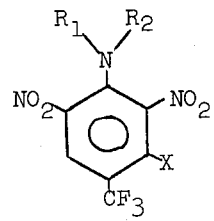

wherein X is halogen, $R_1$ is hydrogen, alkyl, alkenyl, or alkynyl, and $R_2$ is alkyl, alkenyl, or alkynyl, said alkyl, alkenyl, and alkynyl groups being unsubstituted or having halo, hydroxy, or lower alkoxy substituents.

2. A compound according the claim 1 in which X is chlorine or bromine.

3. A compound according to claim 2 in which said $R_1$ and $R_2$ are lower alkyl.

4. A compound according to claim 2 in which said $R_1$ is hydrogen and said $R_2$ is lower alkyl.

5. N,N-diethyl-3-chloro-2,6-dinitro-4-trifluoromethylaniline.

6. N-sec-butyl-3-chloro-2,6-dinitro-4-trifluoromethylaniline.

7. N-(1-methyl-2-methoxyethyl)-3-chloro-2,6-dinitro-4-trifluoromethylaniline.

8. N,N-di-n-propyl-3-chloro-2,6-dinitro-4-trifluoromethylaniline.

9. A compound according to claim 2 in which said $R_1$ and $R_2$ are ethyl.

10. A compound according to claim 2 in which said $R_1$ and $R_2$ are n-propyl.

* * * * *